United States Patent
Han et al.

(10) Patent No.: US 10,856,747 B2
(45) Date of Patent: Dec. 8, 2020

(54) METHOD AND SYSTEM FOR MEASURING HEART RATE IN ELECTRONIC DEVICE USING PHOTOPLETHYSMOGRAPHY

(71) Applicant: Samsung Electronics Co., Ltd., Suwon-si (KR)

(72) Inventors: Jooman Han, Seoul (KR); Jongmin Choi, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 1359 days.

(21) Appl. No.: 14/587,550

(22) Filed: Dec. 31, 2014

(65) Prior Publication Data

US 2015/0190062 A1  Jul. 9, 2015

Related U.S. Application Data

(60) Provisional application No. 61/924,606, filed on Jan. 7, 2014.

(30) Foreign Application Priority Data

Apr. 7, 2014  (KR) ........................ 10-2014-0041446

(51) Int. Cl.
- *A61B 5/11* (2006.01)
- *A61B 5/0205* (2006.01)
- *A61B 5/00* (2006.01)
- *A61B 5/024* (2006.01)

(52) U.S. Cl.
CPC ...... *A61B 5/02055* (2013.01); *A61B 5/02416* (2013.01); *A61B 5/11* (2013.01); *A61B 5/7221* (2013.01); *A61B 5/7278* (2013.01)

(58) Field of Classification Search
CPC ... A61B 5/02055; A61B 5/02416; A61B 5/11; A61B 5/7221; A61B 5/7278
See application file for complete search history.

(56) References Cited

U.S. PATENT DOCUMENTS

| | | |
|---|---|---|
| 2003/0212336 A1 | 11/2003 | Lee et al. |
| 2004/0220483 A1 | 11/2004 | Yeo et al. |
| 2004/0225207 A1 | 11/2004 | Bae et al. |
| 2010/0298728 A1 | 11/2010 | Addison et al. |
| 2011/0077486 A1* | 3/2011 | Watson ................. A61B 5/021 600/324 |
| 2011/0224507 A1 | 9/2011 | Banet et al. |

(Continued)

FOREIGN PATENT DOCUMENTS

| | | |
|---|---|---|
| EP | 1354553 A1 | 10/2003 |
| KR | 10-2003-0081903 A | 10/2003 |

(Continued)

OTHER PUBLICATIONS

Korean Office Action with English translation dated Aug. 28, 2020; Korean Appln. No. 10-2014-0041446.

*Primary Examiner* — Mark D Remaly
(74) *Attorney, Agent, or Firm* — Jefferson IP Law, LLP

(57) ABSTRACT

A method and a system for processing a heart rate (HR) in an electronic device are provided. The method includes detecting a photoplethysmography (PPG) signal, producing a first HR from the detected PPG signal, producing a second HR from the detected PPG signal, determining a resultant HR by analyzing the first HR and the second HR, and displaying the resultant HR.

7 Claims, 14 Drawing Sheets

(56) References Cited

U.S. PATENT DOCUMENTS

| | | | |
|---|---|---|---|
| 2012/0190949 A1 | 7/2012 | McCombie et al. | |
| 2012/0203080 A1 | 8/2012 | Kim et al. | |
| 2013/0069780 A1 | 3/2013 | Tran et al. | |
| 2013/0183646 A1* | 7/2013 | Lusted | G09B 19/00 434/236 |
| 2014/0213858 A1 | 7/2014 | Presura et al. | |

FOREIGN PATENT DOCUMENTS

| | | |
|---|---|---|
| KR | 10-2004-0067240 A | 7/2004 |
| KR | 10-2004-0095489 A | 11/2004 |
| KR | 10-0997444 B1 | 11/2010 |
| WO | 2013038296 A1 | 3/2013 |

\* cited by examiner

METHOD AND SYSTEM FOR MEASURING HEART RATE IN ELECTRONIC DEVICE USING PHOTOPLETHYSMOGRAPHY

CROSS-REFERENCE TO RELATED APPLICATION(S)

This application claims the benefit under 35 U.S.C. § 119(e) of a U.S. provisional patent application filed on Jan. 7, 2014 in the U.S. Patent and Trademark Office and assigned Ser. No. 61/924,606, and under 35 U.S.C. § 119(a) of a Korean patent application filed on Apr. 7, 2014 in the Korean Intellectual Property Office and assigned Serial number 10-2014-0041446, the entire disclosure of each of which is hereby incorporated by reference.

TECHNICAL FIELD

The present disclosure relates to a method and a system for measuring a photoplethysmogram, calculating and displaying a heart rate. More particularly, the present disclosure relates to a method and a system for analyzing photoplethysmography (PPG) signals and providing suitable heart rate (HR) output data.

BACKGROUND

Electronic devices have been equipped with various functions, e.g., calculating and measuring a heart rate by photoplethysmography (PPG). Contraction and relaxation of the heart causes the variation of blood flowing in the capillary vessels and this causes the change in volume of the blood vessels. PPG is a technology that illuminates part of the body, measures the amount of light perfused through the body according to the change in volume in the blood vessel, and displays the heart beating pattern in the waveform on a display. PPG may be used for measuring changes in blood volume in the blood vessels or the oxygen saturation of the blood.

Systems of the related art using PPG calculate a heart rate (HR) by measuring an amount of light via a photodiode and converting the measured amount of light to digital signals via an analog-to-digital converter (ADC). In order to start measuring an HR, systems of the related art, however, need a period of time to be stabilized. For example, in order to calculate an HR value, systems of the related art must remove noise of ambient light from PPG signals detected by the sensor and noise caused by their motions, which takes a period of time. Therefore, at a time point that systems of the related art start to measure an HR, they may output an incorrect HR that has been measured while they are stabilized to measure a correct HR.

Therefore, a need exists for a method and a system for analyzing PPG signals and providing suitable HR output data.

The above information is presented as background information only to assist with an understanding of the present disclosure. No determination has been made, and no assertion is made, as to whether any of the above might be applicable as prior art with regard to the present disclosure.

SUMMARY

Aspects of the present disclosure are to address at least the above-mentioned problems and/or disadvantages and to provide at least the advantages described below. Accordingly, an aspect of the present disclosure is to provide a method and a system for analyzing photoplethysmography (PPG) signals and providing suitable heart rate (HR) output data.

In accordance with an aspect of the present disclosure, a method for processing an HR in an electronic device is provided. The method includes detecting a PPG signal, producing a first HR from the detected PPG signal, producing a second HR from the detected PPG signal, determining a resultant HR by analyzing the first HR and the second HR, and displaying the resultant HR.

In accordance with another aspect of the present disclosure, a method for processing an HR in an electronic device is provided. The method includes producing and outputting a first HR from a PPG signal when starting to measure an HR, detecting a motion of the device, correcting the PPG signal according to the detected motion, and producing a second HR from the corrected PPG signal, analyzing the first HR and the second HR, determining, when the second HR is output steadily, the second HR as a resultant HR, and displaying the resultant HR.

In accordance with another aspect of the present disclosure, an electronic device is provided. The electronic device includes an optical sensor for detecting a PPG signal, a sensor unit for detecting a state of a device, a controller for producing a first HR and a second HR from the detected PPG signal, and determining a resultant HR by analyzing the first HR and the second HR, and a display unit for displaying the resultant HR.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which.

Throughout the drawings, it should be noted that like reference numbers are used to depict the same or similar elements, features, and structures.

DETAILED DESCRIPTION

Figure 1:
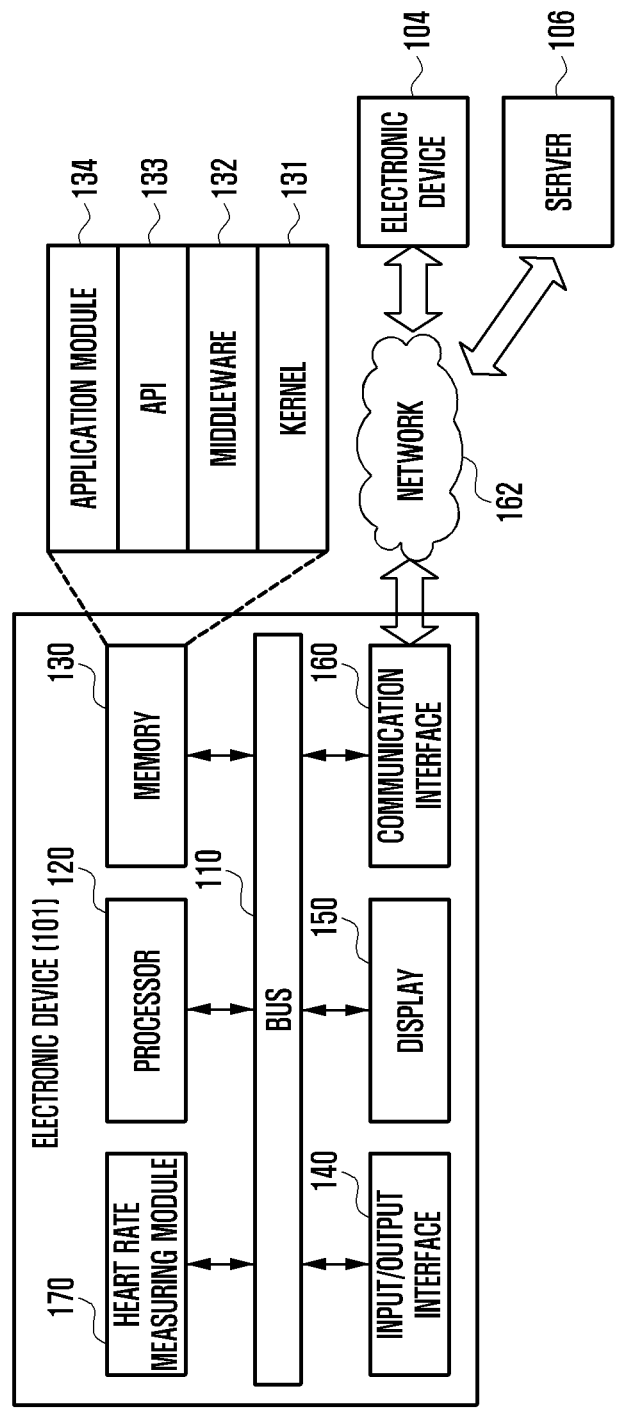
FIG. 1 illustrates a network environment including an electronic device according to an embodiment of the present disclosure.

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

By the term "substantially" it is meant that the recited characteristic, parameter, or value need not be achieved exactly, but that deviations or variations, including for example, tolerances, measurement error, measurement accuracy limitations and other factors known to skill in the art, may occur in amounts that do not preclude the effect the characteristic was intended to provide.

The expressions such as "include" and "may include" which may be used in the present disclosure denote the presence of the disclosed functions, operations, and constituent elements and do not limit one or more additional functions, operations, and constituent elements. In the present disclosure, the terms such as "include" and/or "have" may be construed to denote a certain characteristic, number, step, operation, constituent element, component or a combination thereof, but may not be construed to exclude the existence of or a possibility of the addition of one or more other characteristics, numbers, steps, operations, constituent elements, components or combinations thereof.

In the present disclosure, the expression "and/or" includes any and all combinations of the associated listed words. For example, the expression "A and/or B" may include A, may include B, or may include both A and B.

In the present disclosure, expressions including ordinal numbers, such as "first" and "second," and/or the like, may modify various elements. However, such elements are not limited by the above expressions. For example, the above expressions do not limit the sequence and/or importance of the elements. The above expressions are used merely for the purpose of distinguishing an element from the other elements. For example, a first user device and a second user device indicate different user devices although for both of them the first user device and the second user device are user devices. For example, a first element could be termed a second element, and similarly, a second element could be also termed a first element without departing from the scope of the present disclosure.

In the case where according to which a component is referred to as being "connected" or "accessed" to other component, it should be understood that not only the component is directly connected or accessed to the other component, but also another component may exist between the component and the other component. Meanwhile, in the case where according to which a component is referred to as being "directly connected" or "directly accessed" to other component, it should be understood that there is no component therebetween.

The terms used in the present disclosure are only used to describe specific embodiments, and are not intended to limit the present disclosure.

Unless otherwise defined, all terms including technical and/or scientific terms used herein have the same meaning as commonly understood by one of ordinary skill in the art to which the present disclosure pertains. In addition, unless otherwise defined, all terms defined in generally used dictionaries may not be overly interpreted.

The electronic device according to various embodiments of the present disclosure may be a device including a heart rate measuring function. For example, the electronic device corresponds to a combination of at least one of a smartphone, a tablet Personal Computer (PC), a mobile phone, a video phone, an e-book reader, a desktop PC, a laptop PC, a netbook computer, a Personal Digital Assistant (PDA), a Portable Multimedia Player (PMP), a digital audio player (e.g., a Motion Pictures Expert Group (MPEG-1 or MPEG-2) Audio Layer 3 (MP3) player), a mobile medical device, a camera, or a wearable device. Examples of the wearable device are a head-mounted device (HMD) (e.g., electronic eyeglasses), electronic clothing, an electronic bracelet, an electronic necklace, an appcessory, an electronic tattoo, a smart watch, and the like.

The electronic device according to various embodiments of the present disclosure may be smart home appliances with a heart rate measuring function. Examples of the smart home appliances are a television (TV), a Digital Video Disk (DVD) player, an audio system, a refrigerator, an air-conditioner, a cleaning device, an oven, a microwave oven, a washing machine, an air cleaner, a set-top box, a TV box (e.g., Samsung HomeSync™, Apple TV™, or Google TV™), a game console, an electronic dictionary, an electronic key, a camcorder, an electronic album, or the like.

The electronic device according to various embodiments of the present disclosure may include at least one of medical devices (e.g., Magnetic Resonance Angiography (MRA), Magnetic Resonance Imaging (MRI), Computed Tomography (CT), a scanning machine, an ultrasonic scanning device, and the like), a navigation device, a Global Positioning System (GPS) receiver, an Event Data Recorder (EDR), a Flight Data Recorder (FDR), a vehicle infotainment device, an electronic equipment for ships (e.g., navigation equipment, gyrocompass, and the like), avionics, a security device, a head unit for vehicles, an industrial or home robot, an automatic teller's machine (ATM), a point of sales (POS) system, and the like.

The electronic device according to various embodiments of the present disclosure may include at least one of a furniture or a portion of a building/structure, an electronic board, an electronic signature receiving device, a projector, various measuring instruments (e.g., a water meter, an electric meter, a gas meter and a wave meter), and the like, which are equipped with a heart rate measuring function, respectively. The electronic device according to various embodiments of the present disclosure may also include a combination of the devices listed above. In addition, the electronic device according to various embodiments of the present disclosure may be a flexible device. It is obvious to those skilled in the art that the electronic device according to various embodiments of the present disclosure is not limited to the aforementioned devices.

Hereinafter, electronic devices according to various embodiments of the present disclosure are described with reference to the accompanying drawings. In the description, the term a 'user' may be referred to as a person or a device that uses an electronic device, e.g., an artificial intelligent electronic device.

FIG. 1 illustrates a network environment including an electronic device according to an embodiment of the present disclosure.

Referring to FIG. 1, an electronic device 101 may include a bus 110, a processor 120, a memory 130, an input/output (I/O) interface 140, a display 150, a communication interface 160 and a heart rate measuring module 170.

The bus 110 may be a communication circuit that connects the components to each other and transfers data (e.g., control messages) between the components.

The processor 120 may receive instructions from the components (e.g., the memory 130, the I/O interface 140, the display 150, the communication interface 160, the heart rate measuring module 170, and the like) via the bus 110, decode them and perform corresponding operations or data processing according to the decoded instructions.

The memory 130 may store instructions or data transferred from/created in the processor 120 or the other components (e.g., the I/O interface 140, the display 150, the communication interface 160, the heart rate measuring module 170, and the like). The memory 130 may include programming modules, e.g., a kernel 131, middleware 132, application programming interface (API) 133, application module 134, and the like. Each of the programming modules may be software, firmware, hardware or a combination thereof.

The kernel 131 may control or manage system resources (e.g., the bus 110, processor 120, memory 130, and the like) used to execute operations or functions of the programming modules, e.g., the middleware 132, API 133, and application module 134. The kernel 131 may also provide an interface that can access and control/manage the components of the electronic device 101 via the middleware 132, API 133, and application module 134.

The middleware 132 may make it possible for the API 133 or application module 134 to perform data communication with the kernel 131. The middleware 132 may also perform control operations (e.g., scheduling, load balancing) for task requests transmitted from the application module 134 by methods, for example, a method for assigning the order of priority to use the system resources (e.g., the bus 110, processor 120, memory 130, and the like) of the electronic device 101 to at least one of the applications of the application module 134.

The API 133 is an interface that allows the application module 134 to control functions of the kernel 131 or middleware 132. For example, the API 133 may include at least one interface or function (e.g., instruction) for file control, window control, character control, video process, and the like.

In various embodiments of the present disclosure, the application module 134 may include applications that are related to short message service (SMS)/multimedia messaging service (MMS), email, calendar, alarm, health care (e.g., an application for measuring the blood sugar level, a workout application, and the like), environment information (e.g., atmospheric pressure, humidity, temperature, and the like), and so on. The application module 134 may be an application related to exchanging information between the electronic device 101 and the external electronic devices (e.g., an electronic device 104). The information exchange-related application may include a notification relay application for transmitting specific information to an external electronic device or a device management application for managing external electronic devices.

For example, the notification relay application may include a function for transmitting notification information, created by the other applications of the electronic device 101 (e.g., an SMS/MMS application, an email application, a health care application, an environment information application, and the like), to an external electronic device (e.g., the electronic device 104). In addition, the notification relay application may receive notification information from an external electronic device (e.g., the electronic device 104) and provide it to the user. The device management application can manage (e.g., to install, delete, or update) part of the functions of an external electronic device (e.g., the electronic device 104) communicating with the electronic device 101, e.g., turning on/off the external electronic device, turning on/off part of the components of the external electronic device, adjusting the brightness (or the display resolution) of the display of the external electronic device, and the like, applications operated in the external electronic device or services from the external electronic device, e.g., a call service, a messaging service, and the like.

In various embodiments of the present disclosure, the application module 134 may include applications designated according to attributes (e.g., type of electronic device) of the external electronic device (e.g., the electronic device 104). For example, if the external electronic device is an MP3 player, the application module 134 may include an application related to music playback. If the external electronic device is a mobile medical device, the application module 134 may include an application related to health care. In an embodiment of the present disclosure, the application module 134 may include at least one of an application designated in the electronic device 101 and applications transmitted from external electronic devices (e.g., a server 106, the electronic device 104, and the like).

The I/O interface 140 may receive instructions or data from the user via an I/O system (e.g., a sensor, keyboard or touch screen) and transfers them to the processor 120, memory 130, communication interface 160 or heart rate measuring module 170 through the bus 110. For example, the I/O interface 140 may provide data corresponding to a user's touch input to a touch screen to the processor 120. The I/O interface 140 may receive instructions or data from the processor 120, memory 130, communication interface 160 or heart rate measuring module 170 through the bus 110, and output them to an I/O system (e.g., a speaker or a display). For example, the I/O interface 140 may output voice data processed by the processor 120 to the speaker.

The display 150 may display information (e.g., multimedia data, text data, and the like) on the screen so that the user can view it.

The communication interface 160 may communicate between the electronic device 101 and an external system (e.g., the electronic device 104, the server 106, and the like). For example, the communication interface 160 may connect to a network 162 in wireless or wired mode and communicate with the external system. Wireless communication may include at least one of Wireless Fidelity (Wi-Fi), Bluetooth (BT), near field communication (NFC), GPS or cellular communication (e.g., long term evolution (LTE), LTE-advanced (LTE-A), code division multiple access (CDMA), wideband CDMA (WCDMA), universal mobile telecommunications system (UMTS), wireless broadband (Wi-Bro), global system for mobile communications (GSM), and the like). Wired communication may include at least one of universal serial bus (USB), high definition multimedia interface (HDMI), recommended standard 232 (RS-232), plain old telephone service (POTS), and the like.

In an embodiment of the present disclosure, the network 162 may be a telecommunication network. The telecommunication network may include at least one of a computer network, Internet, Internet of things, telephone network, and the like. The protocol for communication between the electronic device 101 and the external system, e.g., transport layer protocol, data link layer protocol, or physical layer protocol, may be supported by at least one of application module 134, API 133, middleware 132, kernel 131 and communication module 160.

Figure 2:
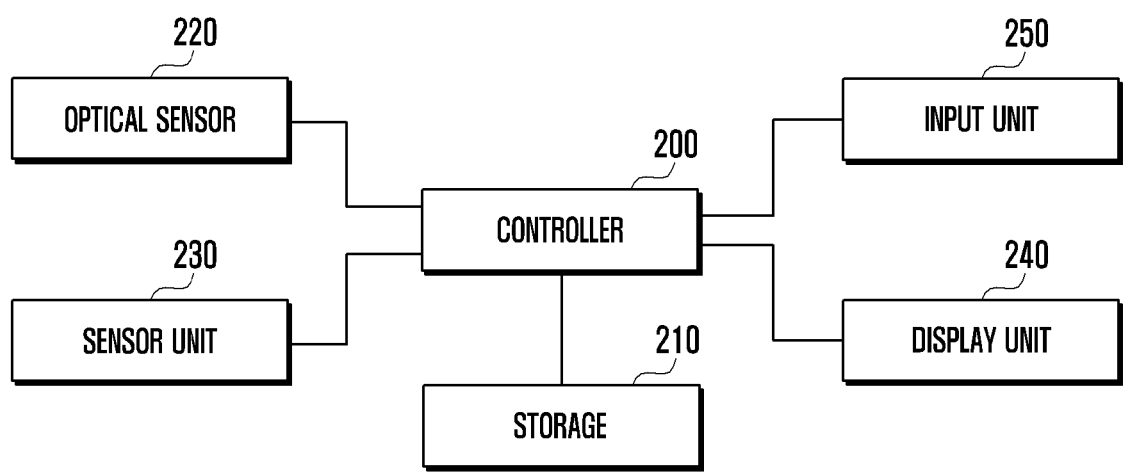
FIG. 2 illustrates a schematic block diagram of an electronic device with a heart rate (HR) measuring module according to an embodiment of the present disclosure.

FIG. 2 illustrates a schematic block diagram of an electronic device with a heart rate (HR) measuring module according to an embodiment of the present disclosure.

Referring to FIG. 2, the electronic device 101 includes a controller 200, a storage 210, an optical sensor 220, a sensor unit 230, a display unit 240 and an input unit 250.

The optical sensor 220 includes a light emitting unit for emitting light to the skin and a light receiving unit for receiving light whose amount is changed according to contraction or relaxation of the blood vessels. The optical sensor 220 can detect changes in the amount of light according to contraction or relaxation of the blood vessels of the skin. The sensor unit 230 may include a sensor for detecting movements of the electronic device 101 and light sensors for detecting brightness surrounding the electronic device 101. The sensor for detecting movements may be a 3-axis accelerometer. If the electronic device 101 is a wearable electronic device, worn on the body, e.g., a watch type of electronic device, it may further include a sensor for detecting whether it is worn on the body. In the following description, the optical sensor 220 is referred to as a photoplethysmography (PPG) sensor.

The controller 200 may produce a first heart rate from a photoplethysmogram measured by the optical sensor 220. In addition, the controller 200 may correct the photoplethysmogram output from the optical sensor 220 according to the movements of the electronic device 101 detected by the sensor unit 230 and then produce a second heart rate from the corrected photoplethysmogram. The controller 200 may determine a heart rate by analyzing the first and second heart rates and display the determined heart rate.

The storage 210 may store data and programs for controlling the operations of the electronic device 101. The storage 210 may also store heart rate values corresponding to photoplethysmograms.

The display unit 240 may display a heart rate according to the control of the controller 200. The input unit 250 may generate instructions for operations of the electronic device 101, key data, and the like. The display unit 240 and input unit 250 may be implemented with a touch screen.

Figure 3A:
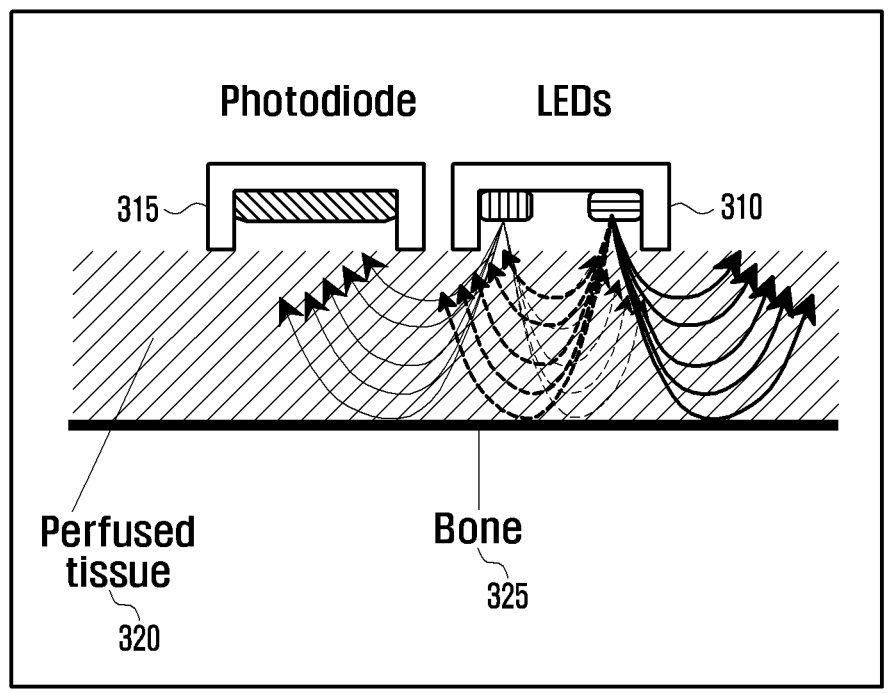
FIG. 3A illustrates a method for measuring a photoplethysmogram using light emitting diodes (LEDs) and a photodiode according to an embodiment of the present disclosure.

FIG. 3A illustrates a method for measuring a photoplethysmogram using light emitting diodes (LEDs) and a photodiode according to an embodiment of the present disclosure.

A photoplethysmogram can be obtained by a PPG that illuminates part of the body, e.g., the fingertip, and the like, with light and measures the change in blood volume of the blood vessels or the oxygen saturation of the blood. For example, when contraction and relaxation of the heart repeats and this causes the change in volume in the capillaries, the optical sensor 220 detects the amount of light according to the change in volume of the blood vessels and generates a PPG signal.

Referring to FIG. 3A, the optical sensor 220 includes a light emitting unit 310 for emitting light and a light receiving unit 315 for receiving light. For example, the light emitting unit 310 and the light receiving unit 315 may be an LED and a photodiode, respectively, which are also hereinafter denoted with reference numbers 310 and 315.

As illustrated in FIG. 3A, when the optical sensor 220 is placed on the finger, it can contact the skin 320 near the bone 325. When the light emitting unit 310 illuminates the skin 320 with the light, the photodiode 315 detects the amount of light from the skin. For example, when the optical sensor 220 tightly contacts the finger, the light from the light emitting unit 310 is diffused and scattered while traveling through a number of layers in the finger and part of the light is incident on the photodiode 315. The optical sensor 220 may be implemented with transmission mode or reflection mode. When the optical sensor 220 is implemented with transmission mode, it may be designed in such a way that the light emitting unit 310 illuminates part of the body (e.g., skin 320, a finger, and the like) with light and the photodiode 315 detects light through the body on the other side. When the optical sensor 220 is implemented with reflection mode, it may be designed in such a way that the light emitting unit 310 illuminates part of the body (e.g., skin 320, a finger, and the like) with light and the photodiode 315 detects light reflected from the body on the same side. The light emitting unit 310 may be a light source emitting green or red light or infrared light.

Figure 3B:
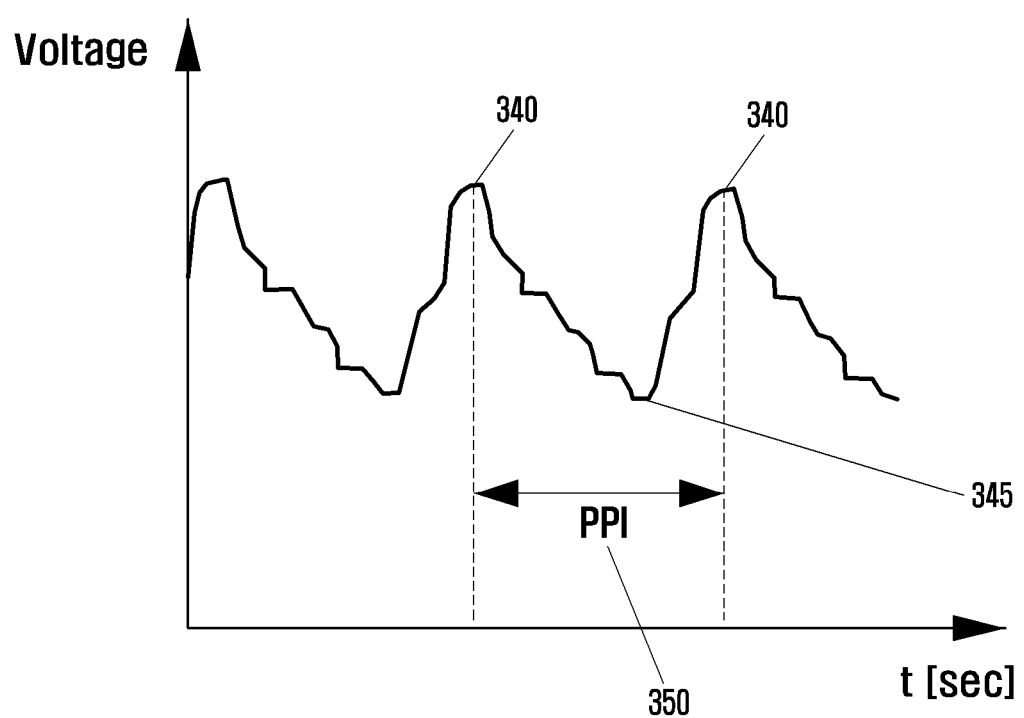
FIG. 3B illustrates a plot of a photoplethysmography (PPG) signal output from an optical sensor, showing a peak-to-peak interval (PPI), according to an embodiment of the present disclosure.

FIG. 3B illustrates a plot of a PPG signal output from an optical sensor, showing a peak-to-peak interval (PPI), according to an embodiment of the present disclosure.

Referring to FIG. 3B, the optical sensor 220 can detect changes in amount of blood in the finger between periods of contraction and relaxation according to a beat rate, as it increases during the contraction showing relatively darker in color and decreases during the relaxation showing lighter in color. Referring to FIG. 3B, the optical sensor 220 outputs a PPG signal showing the variation of light between the period of contraction during which the photodiode 315 detects a relatively small amount of light, showing a point on the plot denoted by reference number 345, and the period of relaxation during which it detects a relatively large amount of light, showing a point of the plot denoted by reference number 340. The controller 200 analyzes the variation of the amount of detected light and outputs a PPG signal. The controller 200 analyzes the PPG signal, detects a PPI from the PPG signal, and determines a heart rate. For example, as shown in FIG. 3B, the controller 200 can determine a heart rate in such a way that it measures an interval 350 (e.g., a period of pulse) between two peaks 340 or two peaks 345 on the plot of the PPG signal and calculates the number of pulses per second.

Figure 3C:
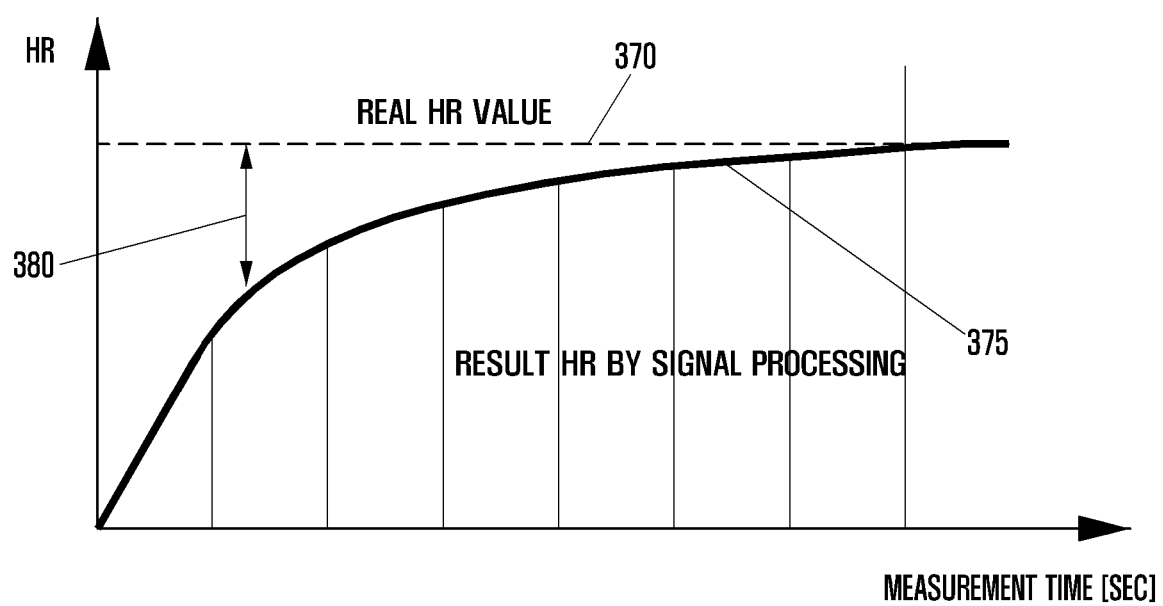
FIG. 3C illustrates a plot that describes a difference between a real HR and an HR measured by an electronic device, according to an embodiment of the present disclosure.

FIG. 3C illustrates a plot that describes a difference between a real HR and an HR measured by an electronic device, according to an embodiment of the present disclosure.

In order to measure a correct HR, the electronic device 101 needs to remove noise caused by the ambient light from a PPG signal output from the optical sensor 220, noise caused by its movements, and the like. To do this, the electronic device 101 needs a period of time to remove noise cause according to the external environment factors and to measure stabilized a PPG signal when measuring a heart rate. For example, referring to FIG. 3C, when the electronic device 101 measures an HR by using an HR value by signal processing in the first heat rate measuring interval, there is a difference 380 between a real HR value 370 and an HR value 375 measured by signal processing at the initial operation time point. Therefore, the electronic device 101 may determine and display an HR by using a PPG signal output from the optical sensor 220 in the first operation interval, and the electronic device 101 may output the HR by using a PPG signal that noise caused by external environment factors and noise caused by the movements is removed from at a time point that the device has been stabilized after a period of time has elapsed.

In various embodiments of the present disclosure, an HR measuring method may include a process for analyzing external environment factors or an adaptive filter processing in order to obtain a stabilized HR value. The more the number of processes increases, the slower the stabilized HR output is produced. An HR may be output by a method employing a relative small number of processes before obtaining a stabilized HR value.

Figure 4:
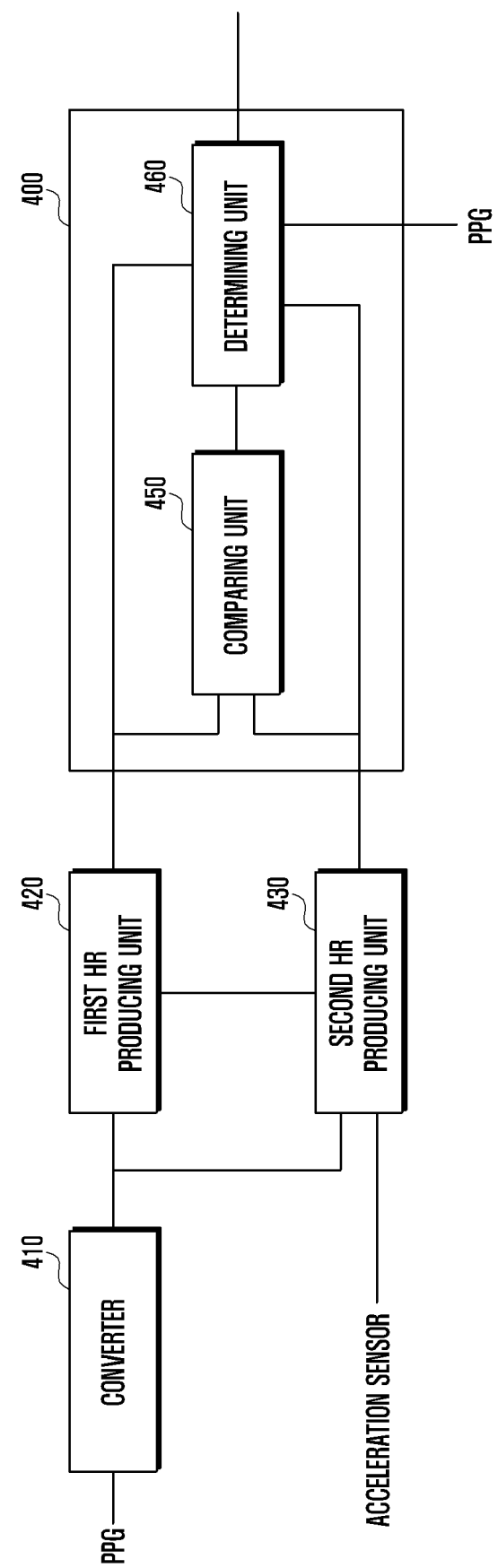
FIG. 4 illustrates a schematic block diagram of a controller of an electronic device according to an embodiment of the present disclosure.

FIG. 4 illustrates a schematic block diagram of a controller of an electronic device according to an embodiment of the present disclosure.

Referring to FIG. 4, the controller 200 may include a converter 410, a first HR producing unit 420, a second HR producing unit 430, and an HR processor 400.

The converter 410 amplifies PPG signals from the optical sensor 220 and processes them to digital signals. The converter 410 may be between the controller 200 and the optical sensor 220. The first HR producing unit 420 calculates a PPI based on the PPG signal from the converter 410 and creates an HR 1 signal by using the PPI. The second HR producing unit 430 filters a motion component of the electronic device 101 output from the sensor unit 230 by using an adaptive filter, applies the filtered result to the PPG signal output from the converter 410 to produce a PPG signal for compensating the motion of the electronic device 101, and creases an HR 2 signal by suing the motion compensating PPG signal. For example, the sensor unit 230 may be an acceleration sensor.

The HR processor 400 may analyze the HR 1 and HR 2 and create and output a resultant HR. The HR processor 400 may analyze a difference between the HR 1 and HR 2 at the initial operation and determine the resultant HR. The electronic device 101 with a heart rate measuring module can produce a PPG signal by using the optical sensor 220. For example, the optical sensor 220 may create a PPG signal from light detected by the photodiode, which is part of light that the LED illustrates a user's skin with and is perfused in the skin. The converter 410 amplifies the PPG signal output from the optical sensor 220 and coverts it to digital data by performing analog-to-digital (AD) conversion. The PPG data may be converted to a compensated PPG data via an algorithm for compensating effects according to motions of the electronic device 101. The HR processor 400 can produce and output an HR signal by using the compensating PPG data.

In various embodiments of the present disclosure, in order to produce and output the HR, the electronic device 101 may include a configuration for producing an HR 1 signal and a configuration for producing an HR 2 signal as a stabilized HR value. The presence of a large difference between HR 1 and HR 2 indicates that a stabilized HR value is not calculated at the initial operation. In that case, the configuration compares HR 1 with HR 2 and determines the resultant HR. For example, if the difference between HR 1 and HR 2 is greater than or equal to a threshold, the configuration displays the HR 1 as an output. If the difference between HR 1 and HR 2 is less than the threshold, which indicates that a stabilized value is being calculated, the configuration displays the HR 2 as an output. After starting displaying the HR 2, the HR processor consecutively calculates an HR 2 and then displays it. In addition, after entering a stable state, the HR processor may continuously display an instant value as an output.

Figure 5A:
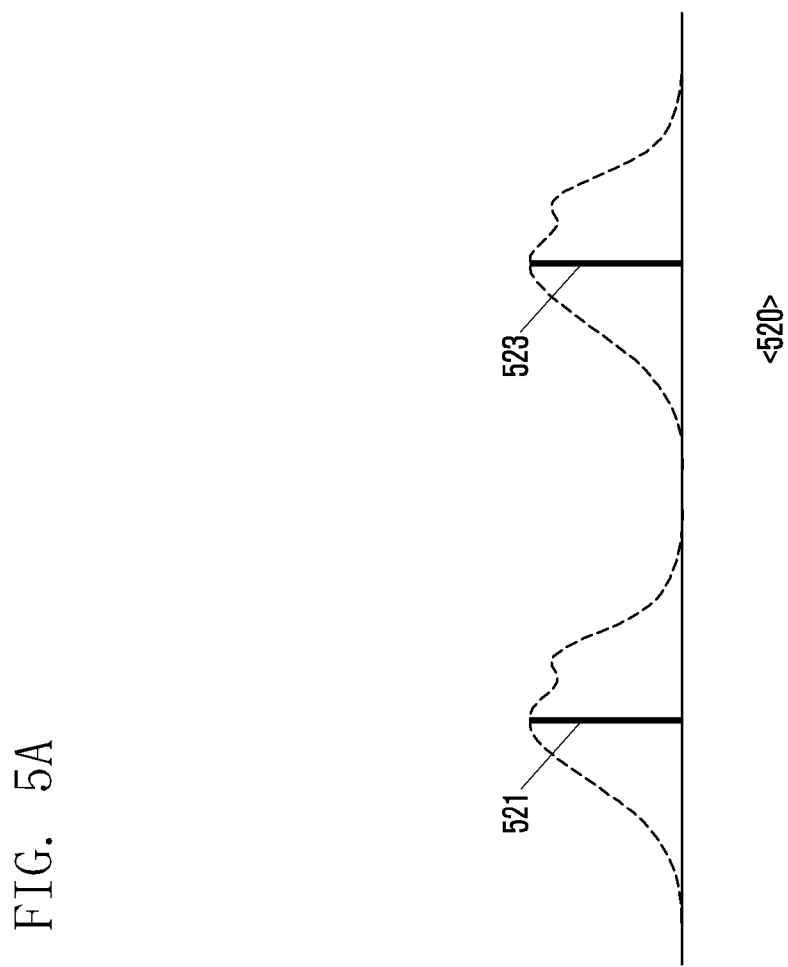
FIGS. 5A and 5B illustrate plots that describe a method for producing an HR 1 in a first HR producing unit according to an embodiment of the present disclosure.
Figure 5B:
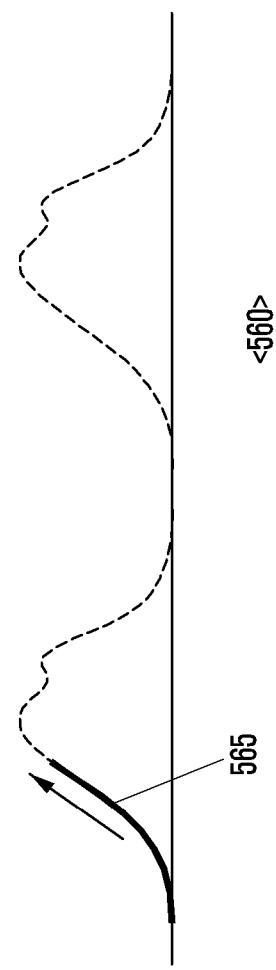
Figure 5B:
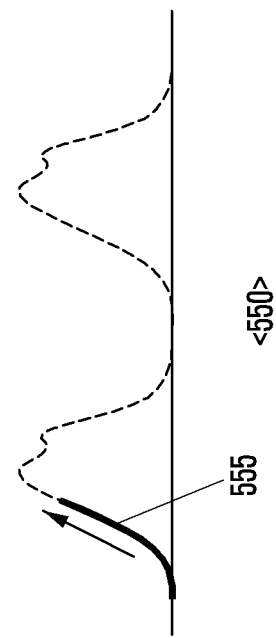

FIGS. 5A and 5B illustrate plots that describe a method for producing an HR 1 in a first HR producing unit according to an embodiment of the present disclosure.

Referring to FIG. 5A, the HR processor 400 can select output of the first HR producing unit 420 by signal processing. The first HR producing unit 420 calculates and produces HR 1 by detecting the peak of the PPG signal (HR raw data) output from the optical sensor 220. The first HR producing unit 420 may include a peak detector. The first HR producing unit 420 may detect peaks of the PPG data, calculate a PPI from the detected peaks, and produce an HR 1. The PPI is an interval on the time domain. If the first HR producing unit 420 operates on the time domain, it does not measure the interval and outputs the major frequency band. The peak detector may be a negative peak detector or a positive peak detector. As shown in plot 510 of FIG. 5A, if peaks 511 and 513 are detected relatively rapidly, the heart rate may be a relatively large value. On the contrary, as shown in plot 520 of FIG. 5A, if peaks 521 and 523 are detected relatively slowly, the heart rate may be a relatively small value.

Referring to FIG. 5B, the HR processor 400 can select output of the first HR producing unit 420 by signal processing. The first HR producing unit 420 produces HR 1 as an HR period by measuring the slope of the PPG data (HR raw data). To this end, the storage 210 may store HR values corresponding to the slopes. The first HR producing unit 420 may include a slope detector. As shown in plots 550 and 560 of FIG. 5B, the slope detector detects the slope for the PPG data, 555 or 565, access the storage 210 for an HR value corresponding to the detected slope, and output an HR 1. The plot 550 of FIG. 5B is a graph with a relatively large slope to describe a case where the HR processor 400 uses a relatively large HR value. The plot 560 of FIG. 5B is a graph with a relatively small slope to describe a case where the HR processor 400 uses a relatively small HR value.

The second HR producing unit 430 receives PPG data from the converter 410 and signals from the sensor unit 230 and removes noises, caused by the movements of the electronic device 101 and the external environment factors, from the PPG data. The second HR producing unit 430 produces HR 2 by calculating the PPG data from which noise is removed. The sensor unit 230 may be a 3-axis accelerometer. Noise caused by the external environment factors may be light from a light source operating at the frequency (e.g., 60 Hz).

The second HR producing unit 430 may produce HR 2 by an adaptive filter using an accelerometer. PPG signals may be distorted by external environment factors (e.g., movements of the electronic device 101, light from ambient light sources, and the like) when measuring PPG. For example, when an examinee is moving, the LED and photodiode, or photo detector (PD) of the optical sensor 220 is also moved. Therefore, the PD may not precisely detect light reflected or back scattered from the skin of the examinee. For example, when the device is in an unsteady state, the optical sensor 220 may detect distorted PPG signals. Therefore, the second HR producing unit 430 can remove background noise from available signals by using an adaptive noise cancellation.

The second HR producing unit 430 may include a motion detector for detecting state signals (e.g., motion components of the electronic device 101) from the output signals of the sensor unit 230 (e.g., an acceleration sensor), an adaptive filter for filtering output signals of the motion detector, a compensator (e.g., a subtracter) for compensating the PPG signal, output from the optical sensor 220, with the output of the adaptive filter (e.g., subtracting the output of the adaptive filter from the PPG signal), and producing a compensated PPG signal, and an HR calculator for calculating the compensated PPG data and HR 2.

When a motion of the electronic device 101 occurs while the optical sensor 220 is measuring a PPG signal, the optical sensor 220 may detect a mixture signal that includes a true signal (or true PPG signal), and motion noise (e.g., distortions that may be caused by movement of the electronic device 101, external light sources, and the like). The sensor unit 230 (e.g., an acceleration sensor with three or more axes) may detect motions of the electronic device 101. The adaptive filter estimates dynamics of distortion process, in response to the measured acceleration, and calculates an estimation of the distorted signal. The estimated distortion can be compensated by the compensator. The compensator can produce a compensated PPG signal by subtracting the distorted distortion from the output of the optical sensor 220. The adaptive filter may include a dynamic model that estimates how to produce a distorted signal component in response to an acceleration value.

As described above, the HR processor 400 may output the HR 1, output from the first HR producing unit 420, as the resultant HR from the initial measurement of HR until the second HR producing unit 430 produces a stabilized HR 2. When the second HR producing unit 430 produces a stabilized HR 2, the HR processor 400 keeps it outputting the HR 2 as the resultant HR.

When outputting an HR at the initial time, the HR processor 400 includes a comparing unit 450, and a determining unit 460. The comparing unit 450 compares the HR 1 with HR 2 and outputs the difference. The determining unit 460 compares the difference with a threshold. The determining unit 460 outputs the HR 1 when the difference is greater than the threshold and HR 2 when the difference is less than the threshold. The HR processor 400 selects and outputs the HR 1 from a time point that it starts measuring HR until the second HR producing unit 430 produces a stabilized HR 2. When the second HR producing unit 430 is stabilized (e.g., the difference between the HR 1 and HR 2 is less than a threshold), the HR processor 400 selects and outputs the HR 2. When the second HR producing unit 430 outputs a stabilized HR 2, the HR processor 400 keeps it outputting the HR 2.

When the HR processor 400 detects a sudden change in condition, it determines the HR 1 output from the first HR producing unit 420 as a resultant HR and outputs it until the second HR producing unit 430 produces a stabilized HR 2. For example, if the electronic device 101 is a wearable wristwatch or a band type of device, it may need a relatively large period of time from a time point that the user puts it on until the second HR producing unit 430 operates in stabilization. In that case, the HR processor 400 may output an HR at the same condition as an HR is first measured. In order to detect a sudden change in condition, the HR processor 400 may use a PPG signal or an additional sensor. For example, if the electronic device 101 is a wearable wristwatch or a band type of device, the HR processor 400 may detect a greater direct current (DC) level of a PPG signal when the user wears it on than when he/she does not. Therefore, when the HR processor 400 measures a DC level of the PPG signal and then detects a sudden change in the level (e.g., as the user takes off or puts of the electronic device 101), it may determine an HR in the same way as it first measures an HR and output it.

As described above, the electronic device 101 for measuring HR according to various embodiments of the present disclosure may include an optical sensor 220 including an LED and a photodiode, a converter 410 for processing signals detected by the optics (i.e., the optical sensor 220), an acceleration sensor 230 for proving motion information, and a controller for operating outputs of the converter 410 and the acceleration sensor 230.

The optical sensor 220 may include a photo detector and infrared (IR) and Red LEDs. The optical sensor 220 may include a photo detector and Green LEDs. The optical sensor 220 may include Green, IR and Red LEDs.

The converter 410 may include an amplifier and an analog-to-digital converter (ADC). The sensor unit 230 may be a 3-axis accelerometer. The controller 200 may include a first HR producing unit 420, a second HR producing unit 430 including a motion algorithm and HR calculation algorithm, and an HR processor 400 for determining HR 1 and HR 2 and a resultant HR and outputting it.

Figure 6:
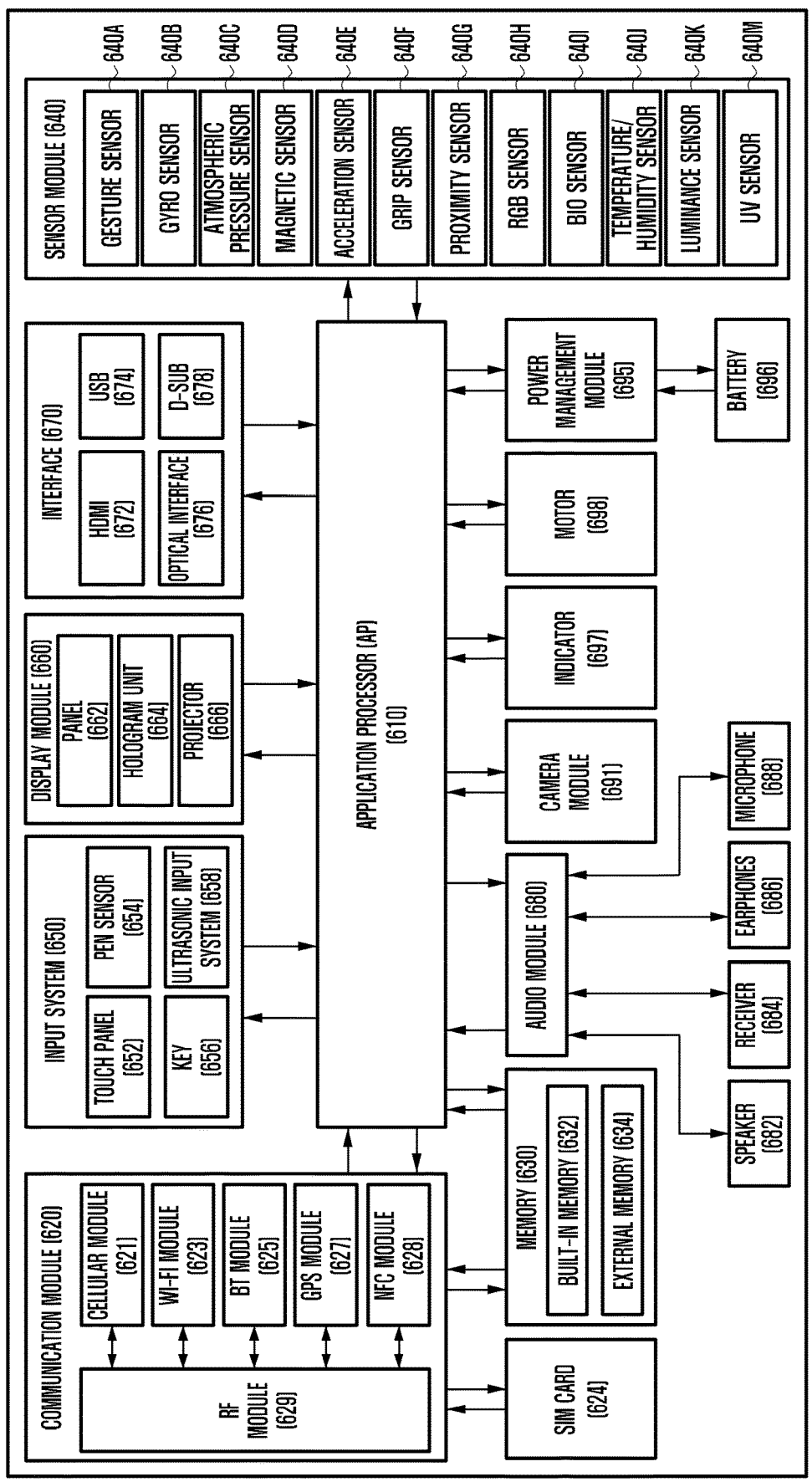
FIG. 6 illustrates a schematic block diagram of an electronic device according to an embodiment of the present disclosure.

FIG. 6 illustrates a schematic block diagram of an electronic device according to an embodiment of the present disclosure. The electronic device may be part or all of electronic device 101 as shown in FIG. 1.

Referring to FIG. 6, the electronic device 101 may include one or more processors of an application processor (AP) 610, a communication module 620, a subscriber identification module (SIM) card 624, a memory 630, a sensor module 640, an input system 650, a display module 660, an interface 670, an audio module 680, a camera module 691, a power management module 695, a battery 696, an indicator 697, and a motor 698.

The AP 610 may control a number of hardware or software components connected thereto by executing the operation system or applications, process data including multimedia data, and perform corresponding operations. The AP 610 may be implemented with a system on chip (SoC). In an embodiment of the present disclosure, the AP 610 may further include a graphic processing unit (GPU).

The communication module 620 (e.g., the communication interface 160) performs communication for data transmission/reception between the other electronic devices (e.g., the electronic device 104, the server 106, and the like) that are connected to the electronic device (e.g., the electronic device 101) via the network. In an embodiment of the present disclosure, the communication module 620 may include a cellular module 621, a Wi-Fi module 623, a BT module 625, a GPS module 627, an NFC module 628 and a radio frequency (RF) module 629.

The cellular module 621 may provide voice call, video call, SMS or Internet service, and the like, via a communication network (e.g., LTE, LTE-A, CDMA, WCDMA, UMTS, Wi-Bro, GSM, and the like). The cellular module 621 may perform identification or authentication for electronic devices in a communication network by using their subscriber identification module (e.g., the SIM card 624). In an embodiment of the present disclosure, the cellular module 621 may perform part of the functions of the AP 610. For example, the cellular module 621 may perform part of the functions for controlling multimedia.

In an embodiment of the present disclosure, the cellular module 621 may include a communication processor (CP). The cellular module 621 may be implemented with, for example, an SoC. Although the embodiment of the present disclosure shown in FIG. 6 is implemented in such a way that the cellular module 621 (e.g., communication processor), the power management module 695, the memory 630, and the like, are separated from the AP 610, it can be modified in such a way that the AP 610 includes at least part of those (e.g., cellular module 621).

In an embodiment of the present disclosure, the AP 610 or the cellular module 621 (e.g., communication processor) may load instructions or data transmitted from at least one of a non-volatile memory or other components, on a volatile memory and then process them. The AP 610 or the cellular module 621 may also store data in a non-volatile memory, which is transmitted from/created in at least one of the other components.

The Wi-Fi module 623, the BT module 625, the GPS module 627 and the NFC module 628 may include processors for processing transmission/reception of data, respectively. Although the embodiment of the present disclosure shown in FIG. 6 is implemented in such a way that the cellular module 621, the Wi-Fi module 623, the BT module 625, the GPS module 627, and the NFC module 628 are separated from each other, it can be modified in such a way that part of those (e.g., two or more) are included in an integrated chip (IC) or an IC package. For example, part of the processors corresponding to the cellular module 621, the Wi-Fi module 623, the BT module 625, the GPS module 627, and the NFC module 628, e.g., a communication processor corresponding to the cellular module 621 and a Wi-Fi processor corresponding to the Wi-Fi 623, may be implemented with an SoC.

The RF module 629 may transmit or receive data, e.g., RF signals. The RF module 629 may include a transceiver, a power amplifier module (PAM), a frequency filter, a low noise amplifier (LNA), and the like. The RF module 629 may also include parts for transmitting/receiving electromagnetic waves, e.g., conductors, wires, and the like, via free space during wireless communication. Although the embodiment of the present disclosure shown in FIG. 6 is implemented in such a way that the cellular module 621, the Wi-Fi module 623, the BT module 625, the GPS module 627, and the NFC module 628 share the RF module 629, it can be modified in such a way that at least one of those transmits or receives RF signals via a separate RF module.

The SIM card 624 may be fitted into a slot of the electronic device 101. The SIM card 624 may include unique identification information, e.g., integrated circuit card identifier (ICCID), or subscriber information, e.g., international mobile subscriber identity (IMSI).

The memory 630 (e.g., the memory 130) may include a built-in memory 632 and/or an external memory 634. The built-in memory 632 may include at least one of a volatile memory, e.g., a dynamic random access memory (DRAM), a static RAM (SRAM), a synchronous DRAM (SDRAM), and the like, a non-volatile memory, e.g., a one-time programmable read only memory (OTPROM), a programmable ROM (PROM), an erasable and programmable ROM (EPROM), an electrically erasable and programmable ROM (EEPROM), a mask ROM, a flash ROM, a NAND flash memory, a NOR flash memory, and the like.

In an embodiment of the present disclosure, the built-in memory 632 may be a Solid State Drive (SSD). The external memory 634 may further include a flash drive, e.g., a compact flash (CF), a secure digital (SD), a micro-SD (micro-SD), a mini-SD (mini-SD), an extreme digital (XD), a memory stick, and the like. The external memory 634 may be functionally connected to the electronic device 101 via various types of interface. In an embodiment of the present disclosure, the electronic device 101 may further include storage devices (or storage media), such as hard drives.

The sensor module 640 may measure physical quantity or detect operation states of the electronic device 101 and convert the measured or detected data to electrical signals. The sensor module 640 may include at least one of a gesture sensor 640A, a gyro sensor 640B, an atmospheric pressure sensor 640C, a magnetic sensor 640D, an acceleration sensor 640E, a grip sensor 640F, proximity sensor 640G, a color sensor 640H (e.g., a red-green-blue (RGB) sensor), a biosensor 640I, a temperature/humidity sensor 640J, a luminance sensor 640K, and a ultra-violet (UV) sensor 640M.

The biosensor 640I may be an HR measuring sensor. The HR measuring sensor may be equipped with an LED and a photodiode. The LED serves as a light source for illuminating a user's skin with light. The photodiode serves a photo detector for detecting part of perfused light from the skin. The detected light is amplified by an amplifier, converted into digital signals via ADC, and transferred to a processor.

The acceleration sensor 640E may detect acceleration information, e.g., motion, and transfer it to the processor. The AP 610 executes an algorithm for compensating a result according to information regarding motion detected by the acceleration sensor and calculates an HR by using the digital signals from the sensor. The AP 610 calculates HR 1 and HR 2, compares HR 1 with HR 2, determines a resultant HR, and outputs it.

The sensor module 640 may also include an e-nose sensor, electromyography (EMG) sensor, an electroencephalogram (EEG) sensor, an electrocardiogram (ECG) sensor, infrared (IR) sensor, a fingerprint sensor, iris sensor, and the like. The sensor module 640 may further include a control circuit for controlling one or more sensors.

The input system 650 may include a touch panel 652, a pen sensor 654 (i.e., a digital pen sensor), a key 656 and an ultrasonic input system 658. The touch panel 652 may detect touches in at least one of a capacitive detecting mode, a pressure detecting mode, an infrared detecting mode, and an ultrasonic detecting mode. The touch panel 652 may further include a control circuit. When the touch panel 652 is designed to operate in capacitive detecting mode, it can detect mechanical/physical touches or proximity of an object. The touch panel 652 may further include a tactile layer. In that case, the touch panel 652 can provide tactile feedback to the user.

The pen sensor 654 (i.e., digital pen sensor) may be implemented in the same or similar way as receiving a user's touch input or by using a separate recognition sheet. The key 656 may include mechanical buttons, optical keys or a key pad. The ultrasonic input system 658 is a device that can detect sounds via a microphone 688 of the electronic device 101 by using an input tool for generating ultrasonic signals and can determine the data. The ultrasonic input system 658 can detect signals in wireless mode. In an embodiment of the present disclosure, the electronic device 101 may receive a user's inputs from an external system (e.g., a computer or server) via the communication module 620.

The display 660 (e.g., display 150) may include a panel 662, a hologram unit 664, or a projector 666. The panel 662 may be implemented with a Liquid Crystal Display (LCD), Active Matrix Organic LEDs (AMOLEDs), or the like. The panel 662 may be implemented in a flexible, transparent, or wearable form. The panel 662 may form a single module with the touch panel 652. The hologram unit 664 shows a three-dimensional image in the air using interference of light. The projector 666 may display images by projecting light on a screen. The screen may be placed, for example, inside or outside the electronic device 101. In an embodiment of the present disclosure, the display module 660 may further include a control circuit for controlling the panel 662, the hologram unit 664, or the projector 666.

The interface 670 may include an HDMI 672, a USB 674, an optical interface 676, a D-subminiature (D-sub) 678, and the like. The interface 670 may also be included in the communication interface 160 shown in FIG. 1. The interface 670 may also include a mobile high-media card (MHL) interface, an SD card, a multi-media card (MMC) interface, an infrared data association (IrDA) standard interface, or the like.

The audio module 680 may make conversion between audios and electrical signals. At least part of the components in the audio module 680 may be included in the I/O interface 140 shown in FIG. 1. The audio module 680 may process audios output from/input to, for example, a speaker 682, a receiver 684, earphones 686, a microphone 688, and the like.

The camera module 691 may take still images or moving images. In an embodiment of the present disclosure, the camera module 691 may include one or more image sensors (e.g., on the front side and/or the back side), a lens, an image signal processor (ISP), a flash (e.g., an LED or a xenon lamp), or the like.

The power management module 695 may manage electric power supplying to the electronic device 101. The power management module 695 may include a power management integrated circuit (PMIC), a charger IC, a battery or fuel gauge, and the like.

The PMIC may be implemented in the form of IC chip or SoC. Charging electric power may be performed in wired or wireless mode. The charger IC may charge a battery, preventing input over-voltage or input over-current from inputting to the battery from a charger. In an embodiment of the present disclosure, the charger IC may be implemented with a wired charging type and/or a wireless charging type. Examples of the wireless charging type of charger IC are a magnetic resonance type, a magnetic induction type, an electromagnetic type, and the like. If the charger IC is implemented with a wireless charging type, it may include an additional circuit for wireless charging, e.g., a coil loop, a resonance circuit, a rectifier, and the like.

The battery gauge may measure the residual amount of battery 696, the level of voltage, the level of current, temperature during the charge. The battery 696 charges electric power and supplies it to the electronic device 101. The battery 696 may include a rechargeable battery or a solar battery.

The indicator 697 shows states of the electronic device 101 or of the parts (e.g., AP 610), e.g., a booting state, a message state, a recharging state, and the like. The motor 698 converts an electrical signal into a mechanical vibration. Although it is not shown, the electronic device 101 may include a processor for supporting a mobile TV, e.g., a GPU. The mobile TV supporting processor may process media data that comply with standards of digital multimedia broadcasting (DMB), digital video broadcasting (DVB), media flow, and the like.

Each of the elements/units of the electronic device 101 according to the present disclosure may be implemented with one or more components, and be called different names according to types of electronic devices. The electronic device 101 according to the present disclosure may include at least one element described above. The electronic device 101 may be modified in such a way as to remove part of the elements or include new elements. In addition, the electronic device 101 according to the present disclosure may also be modified in such a way that parts of the elements are integrated into one entity that performs their original functions.

In various embodiments of the present disclosure, the electronic device 101 may include an optical sensor for detecting a PPG signal, a sensor unit for detecting states of the device, a controller for producing a first HR and a second HR from the measured PPG signal, analyzing the first HR and the second HR, and determining an HR based on the analysis of the first HR and the second HR, and a display unit for displaying the determined HR.

The controller may include a first HR producing unit for producing a first HR from the PPG signal, a second HR producing unit, and an HR processor for comparing and analyzing a first HR and a second HR.

The HR processor may include a comparator for comparing the absolute value of the difference between a first HR and a second HR (i.e., analyzed value) with a threshold, and a determining unit for outputting the first HR when the absolute value of the difference (the analyzed value) is greater than the threshold and the second HR when the absolute value is less than the threshold.

The optical sensor may include a light emitting unit for illuminating the skin with light to measure the PPG signal, and a light receiving unit for receiving light from the skin, varied according to contraction and relaxation of the blood vessels.

The first HR producing unit may detect peaks of the PPG signal, obtain a PPI between the peaks, calculate the PPI in a threshold time and produce a first HR based on the calculation of the PPI.

The first HR producing unit may further include a memory for storing HR values corresponding to the slopes of the PPG signal. The first HR producing unit may detect a slope of the PPG signal and determine an HR, stored in the memory, corresponding to the measured slope.

The second HR producing unit may include a state detector for detecting a state of the device from signals output from the sensor unit, an adaptive filter for applying the detected state of the device, a compensator for producing a compensated PPG by correcting the PPG signal by using the adaptive filter, and a second HR calculator for analyzing the compensated PPG and calculating a second HR based on the analysis.

The state detector may include at least one of an acceleration sensor, a temperature sensor, and a luminance sensor.

The controller keeps outputting the second HR after determining the resultant HR as the second HR. The controller determines the first HR as the resultant HR when the change in level of the PPG signal exceeds a threshold.

The controller may determine the second HR and continuing to output the second HR.

The controller may analyze the PPG signal while outputting the second HR. The controller may determine the first HR as a resultant HR when the change in level of the PPG signal exceeds a threshold.

Figure 7:
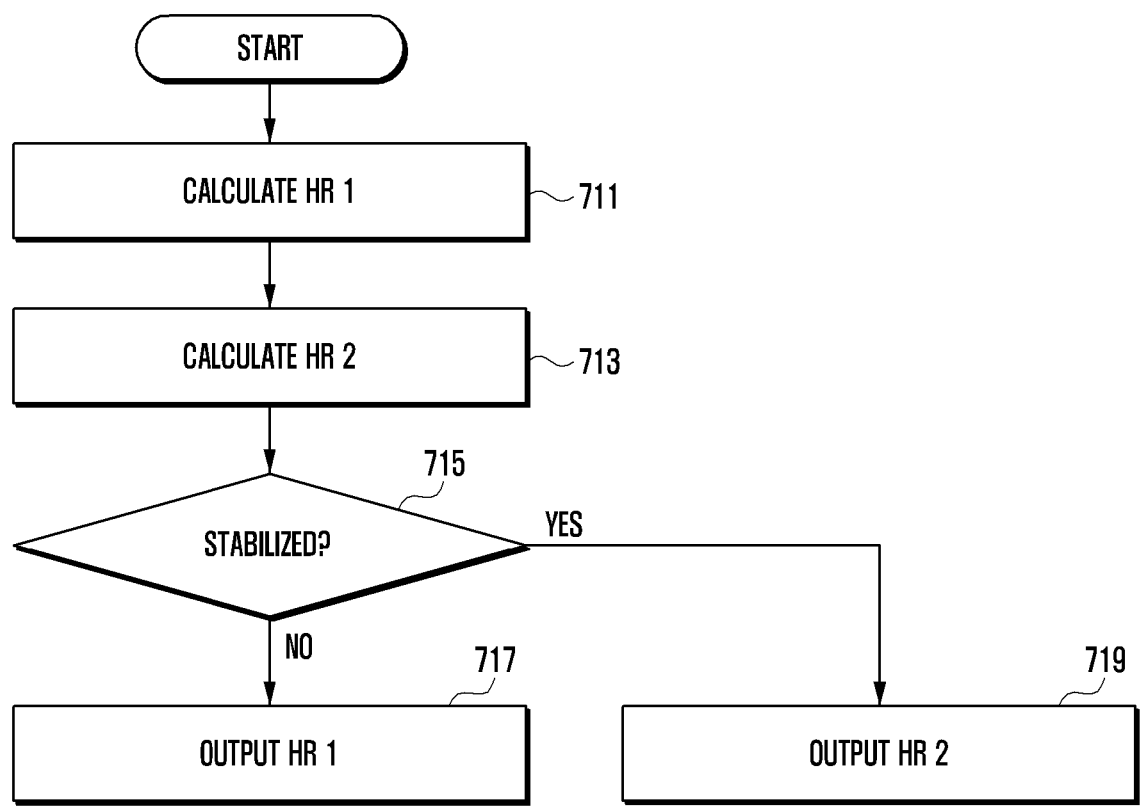
FIG. 7 is a flowchart illustrating a method for measuring an HR in an electronic device according to an embodiment of the present disclosure.

FIG. 7 is a flowchart illustrating a method for measuring an HR in an electronic device according to an embodiment of the present disclosure.

Referring to FIG. 7, the controller 200 produces (i.e., calculates) HR 1 by using PPG signals from the optical sensor 220 at operation 711. The controller 200 produces HR 2 by using PPG signals from the optical sensor 220 and output signals of the sensor unit 230 at operation 713. The controller 200 determines whether the device is stabilized at operation 715. When the electronic device 101 starts to measure an HR, the controller 200 calculates a difference between the HR 1 and HR 2 and compares the difference with a threshold. When the controller 200 ascertains that the difference is greater than the threshold, it concludes that the device is not stabilized. On the contrary, when the controller 200 ascertains that the difference is less than or equal to the threshold, it concludes that the device is stabilized. In addition, the controller 200 measures a period of time from the initial time point for measurement of an HR to a time point that the second HR producing unit 430 outputs a stabilized HR 2. When the controller 200 ascertains that the period of time has elapsed, it concludes that the device is stabilized. Therefore, when the controller 200 ascertains that the device is not stabilized at operation 715, it outputs the HR 1 at operation 717. On the contrary, when the controller 200 ascertains that the device is stabilized at operation 715, it outputs the HR 2 at operation 719.

In addition, when the device experiences a rapid movement from a steady state, it may be in an unsteady state. For example, if the electronic device 101 is a wearable device and the user takes it off or puts it on, the PPG signal generated by the optical sensor 220 may be seriously distorted. In that case, the second HR producing unit 430 cannot completely correct the distortion from a motion component. For example, if the electronic device 101 is removed from/applied to the user's skin or the electronic device 101 contacting the user's skin is shaken according to a user's movement, it may be in an unsteady state. The DC level of the PPG signal detected by the optical sensor 220 may be varied according to the motions of the electronic device 101 (e.g., contacting the skin, closely contacting the skin, spacing apart from the skin at a certain distance, and the like). When the controller 200 ascertains that the DC level of the PPG signal is varied relatively largely, it may conclude that the electronic device is in an unsteady state, as at operation 715. In that case, the controller 200 outputs the HR 1 at operation 717.

Figure 8:
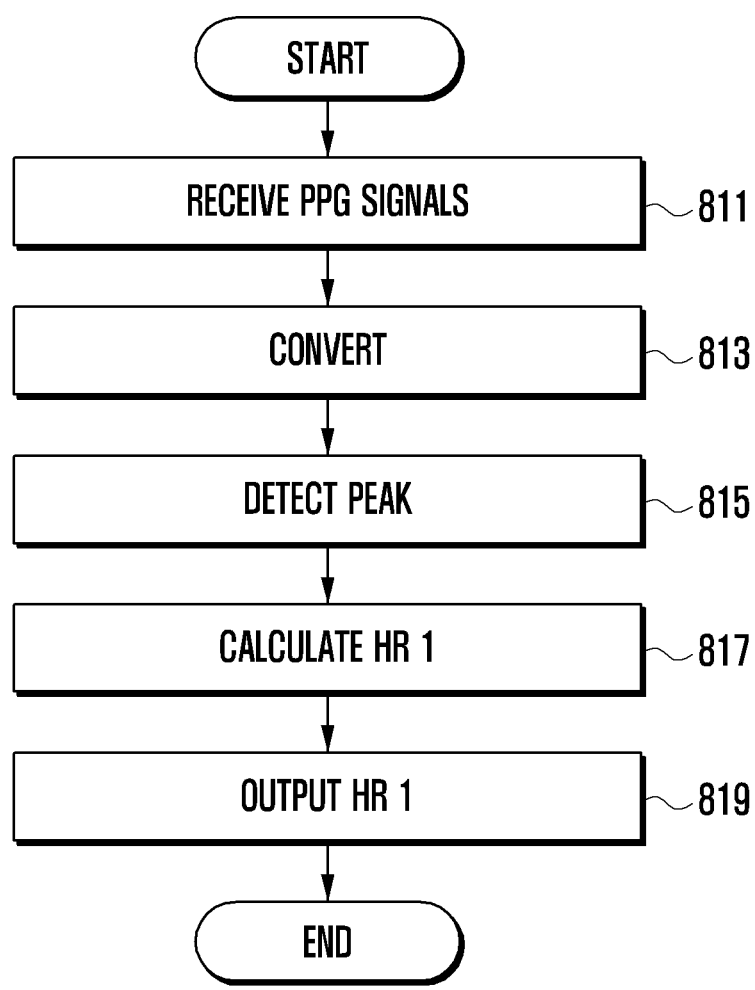
FIG. 8 is a flowchart illustrating a method for calculating an HR by using PPG signals in an electronic device according to an embodiment of the present disclosure.

FIG. 8 is a flowchart illustrating a method for calculating an HR by using a PPG signal in an electronic device according to an embodiment of the present disclosure. The method includes operations for detecting peaks from a PPG signal and producing an HR.

Referring to FIG. 8, the electronic device 101 receives a PPG signal from the optical sensor 220 at operation 811. The electronic device 101 amplifies the PPG signal and converts it to digital data at operation 813. Operations 811 and 813 may be processed by a signal processor (e.g., an analog signal processor) between the controller 200 and the optical sensor 220. The controller 200 detects peaks from the PPG data at operation 815. The controller 200 calculates a PPI from the peaks and produces an HR 1 at operation 817. When the controller 200 ascertains that the device is not stabilized, it outputs the HR 1 at operation 819.

The controller 200 can calculate an HR 1 by using peaks detected from PPG data at operation 815 or slopes detected from the PPG data. The method for calculating an HR 1 by using peaks includes operations for detecting peaks from the PPG data, calculating an interval (e.g., frequency) from the detected peaks, i.e., PPI, and producing an HR 1. The peak detecting method may be a negative peak detection or positive peak detection. If peaks are detected relatively rapidly, the heart rate may be a relatively large value. On the contrary, if peaks are detected relatively slow, the heart rate may be a relatively small value. The method for calculating an HR 1 by using slopes includes operations for measuring slopes from the PPG data (HR raw data), determining an HR period, and producing the determined HR as an HR 1. For example, the controller 200 detects a slope from the PPG data, accesses the storage 210 for an HR value corresponding to the detected slope, and outputs the HR as an HR 1. If the slope of PPG data is relatively steep, the HR 1 may be a relatively large value. On the contrary, if the slope is relatively gentle, the HR 1 may be a relatively small value.

Figure 9:
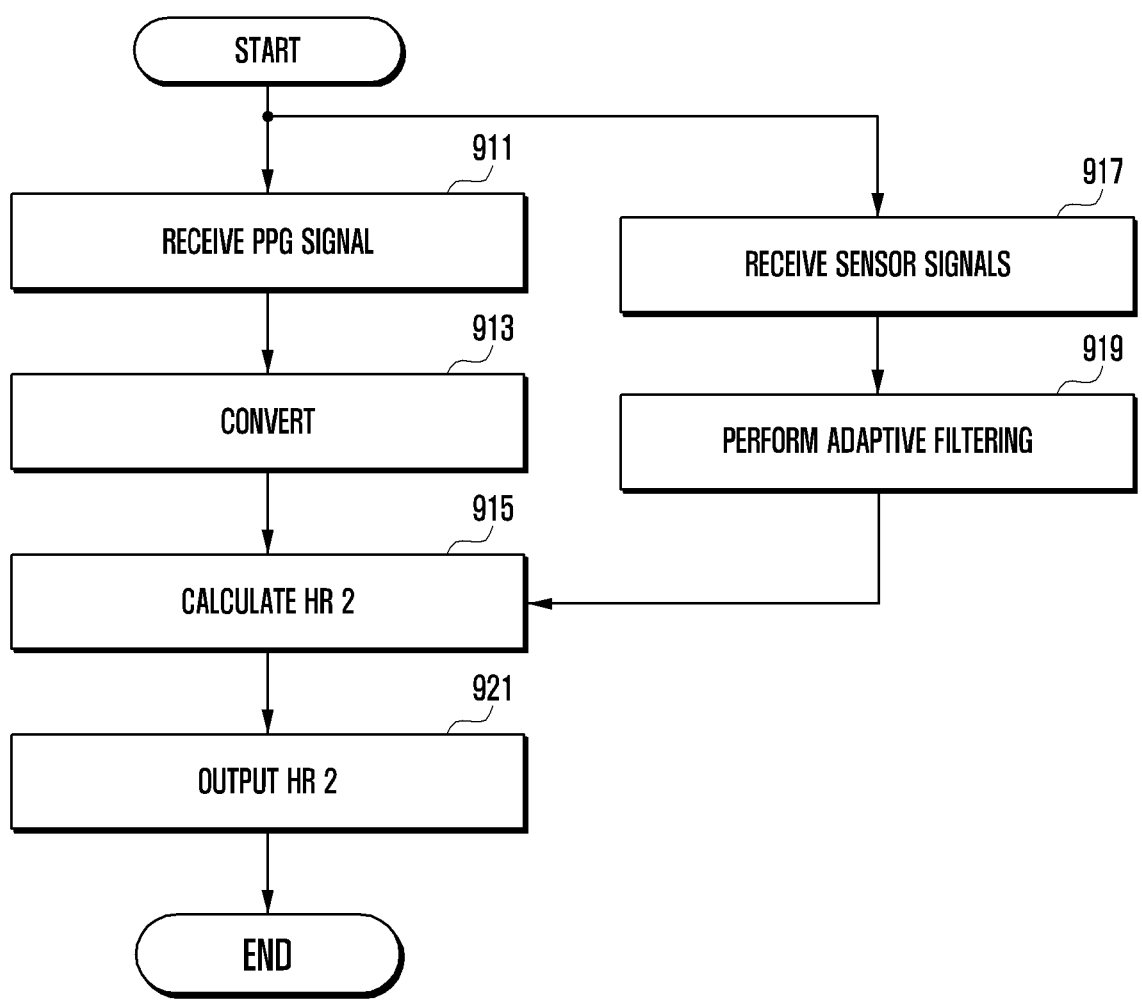
FIG. 9 is a flowchart illustrating a method for calculating an HR by using a PPG signal and a sensor in an electronic device according to an embodiment of the present disclosure.

FIG. 9 is a flowchart illustrating a method for calculating an HR by using a PPG signal and a sensor in an electronic device according to an embodiment of the present disclosure.

Referring to FIG. 9, the electronic device 101 receives a PPG signal from the optical sensor 220 at operation 911. The electronic device 101 amplifies the PPG signal and converts it to digital data at operation 913. Operations 911 and 913 may be processed by a signal processor (e.g., an analog signal processor) between the controller 200 and the optical sensor 220. The PPG signal output from the optical sensor 220 may be a mixture signal that includes a true PPG signal and motion noise. In order to remove motion noise from the mixture signal, the controller 200 receives output signals from the sensor unit 230 (e.g., a 3-axis accelerometer) and detects a motion of the device at operation 917. The controller 200 estimates dynamics of the distortion process in response to the measured acceleration and calculates an estimation of the distorted signal at operation 919. Thereafter, the controller 200 produces compensated PPG data by subtracting the estimation of the distorted signal from the PPG data, and produces an HR 2 by calculating the compensated PPG data at operation 915. Thereafter, the controller 200 outputs the HR 2 if the device is in a steady state at operation 921.

Figure 10:
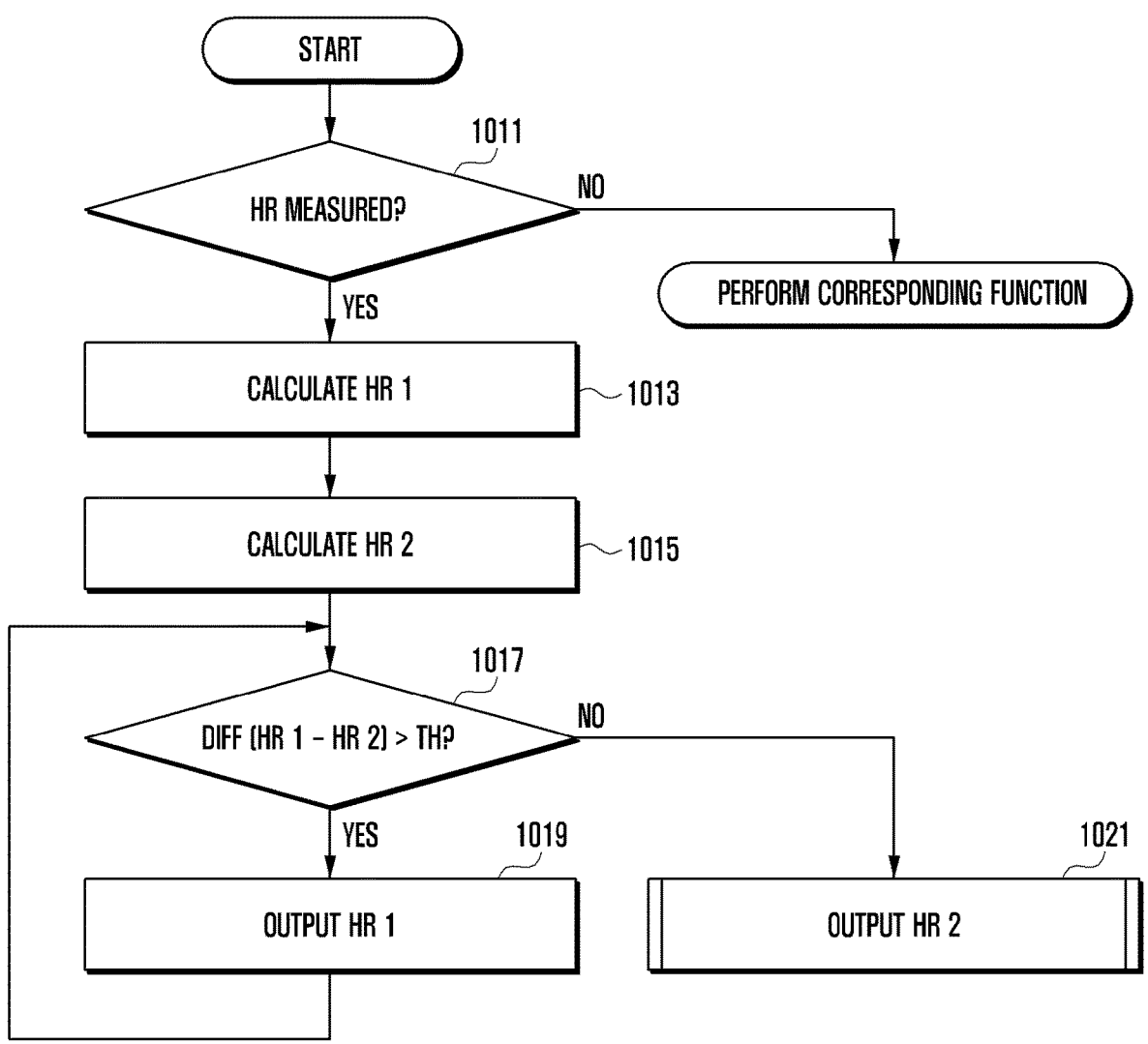
FIG. 10 is a flowchart illustrating a method for measuring an HR in an electronic device according to an embodiment of the present disclosure.

FIG. 10 is a flowchart illustrating a method for measuring an HR in an electronic device according to an embodiment of the present disclosure.

Referring to FIG. 10, when a request is made to measure an HR, the controller 200 detects the request at operation 1011, and calculates HR 1 and HR 2 by performing the following operations 1013 and 1015. The HR 1 may be an HR calculated by using a PPG signal output from the optical sensor 220. The HR 2 may be an HR calculated by using a compensated PPG signal that is created by correcting a distortion caused by the motion component of the device. The controller 200 calculates a difference between the HR 1 and HR 2 and compares the difference with a threshold to determine a state of the device at operation 1017. When the controller 200 ascertains that the difference is greater than the threshold at operation 1017, it concludes that the device is in an unsteady state and outputs the HR 1 at operation 1019. For example, if the device is not stabilized, the controller 200 outputs the HR 1. If the device is stabilized and outputs a stabilized value, the controller 200 ascertains that the difference is less than the threshold at operation 1017 and outputs an HR 2. For example, when the device is stabilized, the controller 200 can detect the stabilization of the device at operation 1017 and continuing to output the HR 2 at operation 1021. When the controller 200 receives a request to measure an HR, it calculates HR 1 and HR 2. An HR 2 calculated at an initial time, such as when the device is in an unsteady state, cannot generate a stabilized signal. The states of the device may depend on motions of the device, temperature, an amount of light surrounding the device, a sudden change in output value of the PPG sensor, and the like. The controller 200 may display an HR 1 by using a PPG signal at the initial time, such as when an HR is not measured steadily because the device is not stabilized. The controller 200 may display an HR 2 calculated when the device is in a steady state.

Figure 11:
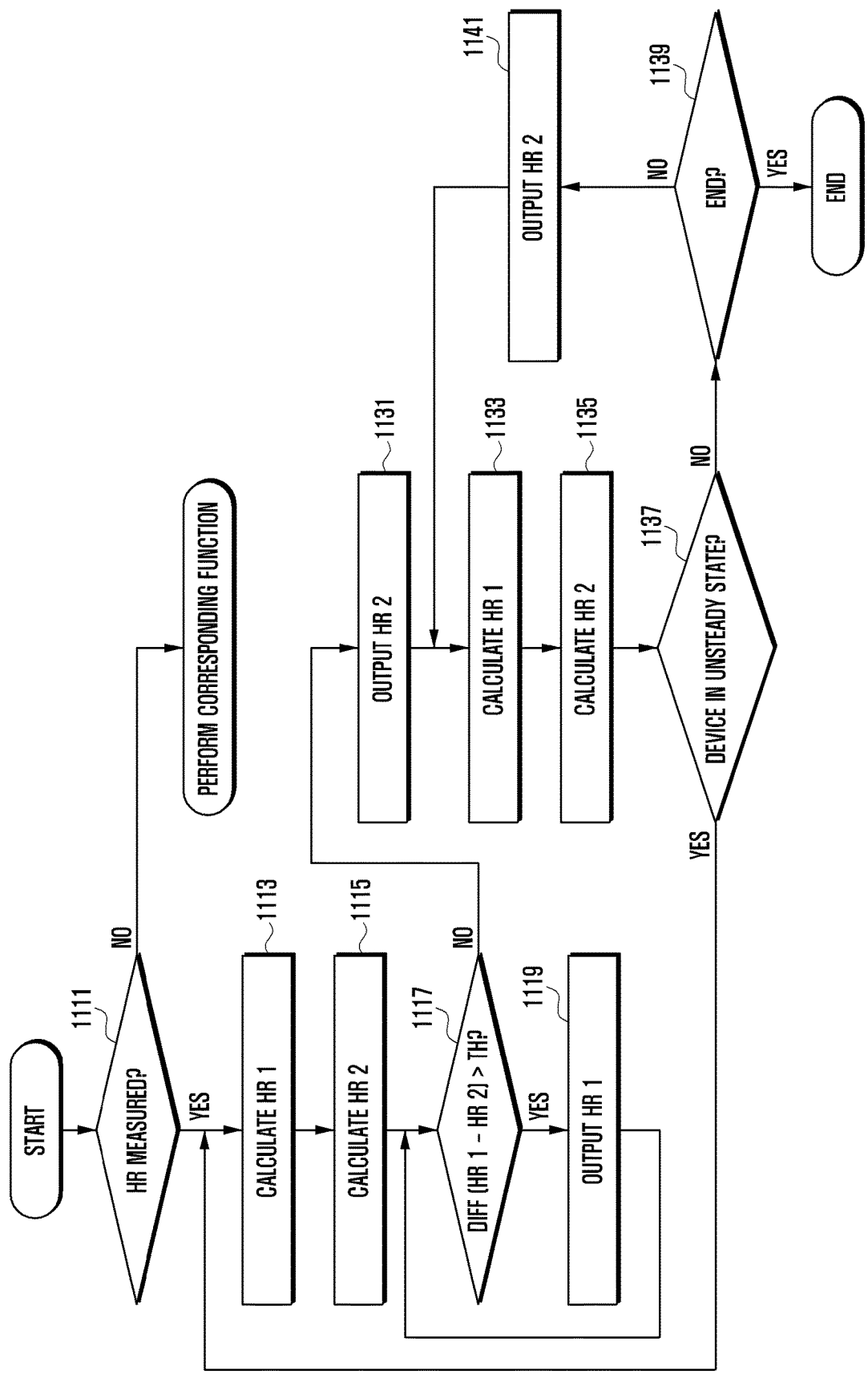
FIG. 11 is a flowchart illustrating a method for measuring an HR in an electronic device according to an embodiment of the present disclosure.

FIG. 11 is a flowchart illustrating a method for measuring an HR in an electronic device according to an embodiment of the present disclosure.

Referring to FIG. 11, operations 1111 to 1119 are performed in the same manner as operations 1011 to 1019 shown in FIG. 10. When the controller 200 ascertains that the device is stabilized at operation 1117, it outputs the HR 2 at operation 1131. For example, the controller 200 calculates a difference between HR 1 and HR 2 and compares the absolute value of the difference with a threshold (Th), i.e., |Diff(HR 1−HR 2)|>Th, at operation 1117. When the difference is greater than the threshold, the controller 200 concludes that the device is in an unsteady state and outputs/displays the HR 1 at operation 1119. On the contrary, when the difference is less than or equal to the threshold, the controller 200 concludes that the device is in a steady state and outputs/displays the HR 2 at operation 1131.

When the controller 200 ascertains that the device is in a steady state, it keeps outputting the HR 2. While the HR 2 is outputting, the controller 200 may produce the HR 1 and HR 2 at operations 1133 and 1135.

Thereafter, the controller 200 determines whether the device is in a steady sate at operation 1137. The determination is to output, when the device is turned to an unsteady state while outputting the HR 2, the HR 1 until the HR 2 is produced steadily. The conditions for determining a state of the device may be motions of the device, temperature, an amount of light surrounding the device, change in output value of the PPG sensor, and the like. For example, if the electronic device 101 is a wearable electronic device, worn on the body, e.g., a watch type of electronic, it may need a relatively large period of time from a time point that the user puts it on until it operates in stabilization.

When the controller 200 detects a sudden change in motion of the device by an acceleration sensor at operation 1137, it may output an HR in the same condition that the HR is measured at the initial time point. Detecting a sudden change in conditions may be performed by a PPG signal or an additional sensor. For example, if the electronic device 101 is a wearable watch, the controller 200 may detect a greater DC level of a PPG signal when the user wears it on than when he/she does not.

When the controller 200 detects a sudden change in the detected DC level of the PPG signal (e.g., a case the electronic device 101 is taken off or put on), it concludes that the device is in an unsteady state. When the device is turned to an unsteady state, the controller 200 detects the unsteady state of the device at operation 1137 and returns to operation 1113. Therefore, the electronic device 101 may determine and output an HR in the same way as it measures an HR at the initial time.

On the contrary, when the controller 200 ascertains that the device is still in a steady state at operation 1137, it keeps outputting the HR 2 at operation 1141.

In addition, the electronic device 101 may further include a temperature sensor for detecting the ambient temperature. When the controller 200 detects a sudden change in temperature of the temperature sensor (e.g., a case where the device is moved from a cold environment to a warm one, or from outdoors to indoors in winter) at operation 1137, it may perform corresponding operations described above.

In addition, the electronic device 101 may further include a luminance sensor for detecting an amount of ambient light. When the controller 200 detects a sudden change in amount of ambient light at operation 1137, it may perform corresponding operations described above. In addition, when the controller 200 detects a sudden change in output value of the PPG sensor, it concludes that the electronic device 101 is in an unsteady state. The controller 200 may repeat the operations until the HR measuring operation is terminated. When the controller 200 receives a request to terminate the HR measuring operation at operation 1139, it terminates the HR measuring operation.

The electronic device 101 includes an optical sensor (i.e., a PPG sensor or a sensor for measuring a heart rate) and may measure a heart rate by using PPG. In various embodiments of the present disclosure, the methods output an HR 1 until stabilized HR values are obtained and an HR 2 when a stabilized HR 2 is obtained. Therefore, the HR measuring system can minimize the possibility of providing incorrect information regarding an HR that largely differs from a true HR from when the device is in an unsteady state until the true HR is displayed.

In various embodiments of the present disclosure, the HR processing method may include measuring a PPG signal, producing a first HR from the measured PPG signal, producing a second HR from the measured PPG signal, determining a resultant HR by analyzing the first HR and the second HR, and displaying the resultant HR.

The determination of a resultant HR may include comparing an absolute value of the difference between the first HR and the second HR with a threshold, determining the first HR as the resultant HR when the absolute value of the difference is greater than the threshold, and determining the second HR as the resultant HR when the absolute value of the difference is less than the threshold.

The determination of a resultant HR may further include continuing to output the second HR after determining the second HR as a resultant HR.

The determination of a resultant HR may further include analyzing the PPG signal while outputting the second HR, and determining the first HR as the resultant HR when the change in level of the PPG signal exceeds a threshold.

The production of a first HR may include converting the change in level of the PPG signal to a frequency value, and producing a first HR by analyzing the frequency value in a threshold time.

The production of a first HR may include detecting peaks of the PPG signal, detecting a PPI between the peaks, and producing a first HR by the PPI. The detection of a PPI may include detecting an interval between positive peaks or negative peaks of the PPG signal.

The production of a first HR may include measuring a slope of the PPG signal and determining an HR, stored in the storage, corresponding to the slope, as the first HR. The storage stores HR values corresponding to the slopes.

The production of a second HR may include detecting a state of the device, correcting the PPG signal according to the detected state of the device, and producing a second HR from the corrected PPG signal.

The production of a second HR may include measuring a state of the device, producing an adaptive filter according to the measured state of the device, producing a compensated PPG by correcting the PPG signal by using the adaptive filter, and producing a second HR by the compensated PPG.

The production of a second HR may include measuring a second HR by using an output of an acceleration sensor and/or an output of a temperature sensor.

In various embodiments of the present disclosure, the HR processing method may include producing and outputting a first HR from a PPG signal when starting to measure an HR, detecting a motion of the device, correcting the PPG signal according to the detected motion and producing a second HR from the corrected PPG signal, analyzing the first HR and the second HR, determining, when the second HR is output steadily, the second HR as a resultant HR, and displaying the resultant HR.

The determination of a resultant HR may further include continuing to output the second HR after determining the second HR.

The determination of a resultant HR may further include analyzing, while outputting the second HR, the PPG signal, and determining the first HR as a resultant HR when the change in level of the PPG signal exceeds a threshold.

As described above, the systems and methods according to the various embodiments of the present disclosure can measure an HR by using PPG. The systems and methods can receive a PPG signal from the sensor and display it as a resultant HR until a stabilized HR is obtained. When a stabilized HR is obtained, the systems and methods can output the stabilized HR. The systems and method can minimize the number of displaying incorrect information that largely differs from a true HR until a user's HR is displayed.

In the present disclosure, the terminology '~module' refers to a 'unit' including hardware, software, firmware or a combination thereof. For example, the terminology '~module' is interchangeable with '~unit,' '~logic,' '~logical block,' '~component,' '~circuit,' and the like. A 'module' may be the least unit or a part of an integrated component. A 'module' may be the least unit or a part thereof that can perform one or more functions. A 'module' may be implemented in mechanical or electronic mode. For example, 'modules' according to the various embodiments of the present disclosure may be implemented with at least one of an application specific integrated circuit (ASIC) chip, field-programmable gate array (FPGAs) and a programmable-logic device that can perform functions that are known or will be developed.

At least part of the method (e.g., operations) or system (e.g., modules or functions) according to the various embodiments of the present disclosure can be implemented with instructions as programming modules that are stored in computer-readable storage media. One or more processors (e.g., processor 201) can execute instructions, thereby performing the functions. An example of the computer-readable storage media may be memory 220. At least part of the programming modules can be implemented (executed) by processor 210. At least part of the programming module may include modules, programs, routines, sets of instructions or processes, and the like, in order to perform one or more functions.

Certain aspects of the present disclosure can also be embodied as computer readable code on a non-transitory computer readable recording medium. A non-transitory computer readable recording medium is any data storage device that can store data which can be thereafter read by a computer system. Examples of the non-transitory computer readable recording medium include Read-Only Memory (ROM), Random-Access Memory (RAM), Compact Disc-ROMs (CD-ROMs), magnetic tapes, floppy disks, and optical data storage devices. The non-transitory computer readable recording medium can also be distributed over network coupled computer systems so that the computer readable code is stored and executed in a distributed fashion. In addition, functional programs, code, and code segments for accomplishing the present disclosure can be easily construed by programmers skilled in the art to which the present disclosure pertains.

At this point it should be noted that the various embodiments of the present disclosure as described above typically involve the processing of input data and the generation of output data to some extent. This input data processing and output data generation may be implemented in hardware or software in combination with hardware. For example, specific electronic components may be employed in a mobile device or similar or related circuitry for implementing the functions associated with the various embodiments of the present disclosure as described above. Alternatively, one or more processors operating in accordance with stored instructions may implement the functions associated with the various embodiments of the present disclosure as described above. If such is the case, it is within the scope of the present disclosure that such instructions may be stored on one or more non-transitory processor readable mediums. Examples of the processor readable mediums include a ROM, a RAM, CD-ROMs, magnetic tapes, floppy disks, and optical data storage devices. The processor readable mediums can also be distributed over network coupled computer systems so that the instructions are stored and executed in a distributed fashion. In addition, functional computer programs, instructions, and instruction segments for accomplishing the present disclosure can be easily construed by programmers skilled in the art to which the present disclosure pertains.

Modules or programming modules according to various embodiments of the present disclosure may include one or more components, remove part of them described above, or include new components. The operations performed by modules, programming modules, or the other components, according to the present disclosure, may be executed in serial, parallel, repetitive or heuristic fashion. Part of the operations can be executed in any other order, skipped, or executed with additional operations.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. An electronic device comprising:
an optical sensor configured to detect a photoplethysmography (PPG) signal;
a processor configured to:
produce a first heart rate (HR) and a second HR from the PPG signal, analyze the first HR and the second HR,
compare an analyzed value with a threshold,
determine, if the analyzed value is greater than the threshold, a resultant HR as the first HR, and
determine, if the analyzed value is less than the threshold, the resultant HR as the second HR; and
a display configured to display the resultant HR.

2. The electronic device of claim 1, wherein the optical sensor comprises:
a light emitter configured to illuminate the skin with light to measure the PPG signal; and
a light receiver configured to receive light from the skin, varied according to contraction and relaxation of the blood vessels.

3. The electronic device of claim 1, wherein the processor is further configured to:
detect peaks of the PPG signal,
determine a peak-to-peak interval (PPI) between the peaks, and
produce the first HR by using the PPI.

4. The electronic device of claim 1,
wherein the processor further comprises a memory configured to store HR values corresponding to slopes of the PPG signal, and
wherein the processor is further configured to:
detect a slope of the PPG signal, and
determine the first HR that is stored in the memory based on the measured slope.

5. The electronic device of claim 1, further comprising:
a sensor configured to detect a state of the device;
an adaptive filter configured to apply the state of the device; and
a compensator configured to produce a compensated PPG by correcting the PPG signal by using the adaptive filter,
wherein the processor is further configured to:
analyze the compensated PPG, and
calculate the second HR based on the analysis.

6. The electronic device of claim 5, wherein the sensor comprises at least one of an acceleration sensor, a temperature sensor, and a luminance sensor.

7. The electronic device of claim 1, wherein the processor is further configured to:
continue outputting the second HR after determining the resultant HR as the second HR, and
determine the first HR as the resultant HR when a value of the PPG signal exceeds a threshold.

\* \* \* \* \*